United States Patent [19]

Horton

[11] Patent Number: 4,856,089
[45] Date of Patent: Aug. 8, 1989

[54] COMBINED EYE COVERING AND EAR COVERING ASSEMBLY

[76] Inventor: Lee A. Horton, 272 N. Prospect, Mundelein, Ill. 60060

[21] Appl. No.: 279,288

[22] Filed: Nov. 30, 1988

Related U.S. Application Data

[63] Continuation of Ser. No. 889,747, Jul. 28, 1986, abandoned.

[51] Int. Cl.$^4$ .......................... H04B 1/08; A61F 9/00
[52] U.S. Cl. ........................................... 455/351; 2/10; 2/13; 2/209; 2/452; 381/187
[58] Field of Search ...................... 455/351, 90, 89, 95, 455/100, 344; 381/183, 187; 379/430; 2/423, 6, 10, DIG. 11, 13, 209, 426, 452, 9, 183, 424, 209.3

[56] References Cited

U.S. PATENT DOCUMENTS

| | | | |
|---|---|---|---|
| D. 207,919 | 6/1967 | Fai | 455/344 |
| D. 212,863 | 12/1968 | Roberts | 455/344 |
| 1,117,968 | 11/1914 | Bobory | 2/209 |
| 2,159,435 | 5/1939 | Gribbin | 2/209 |
| 2,246,031 | 6/1941 | Bartiz et al. | 2/209 |
| 3,173,147 | 3/1975 | Gross et al. | 2/452 |
| 3,902,120 | 8/1975 | Dascal et al. | 455/351 |
| 3,943,925 | 3/1976 | Leight | 2/423 |
| 4,317,238 | 3/1982 | Amin | 2/DIG. 11 |
| 4,340,972 | 7/1982 | Heist | 455/351 |
| 4,393,519 | 7/1983 | Nicastro | 2/172 |
| 4,456,797 | 6/1984 | Olsen | 455/351 |
| 4,520,510 | 6/1985 | Daigle | 2/DIG. 11 |
| 4,630,317 | 12/1986 | Brown et al. | 2/DIG. 11 |
| 4,632,104 | 12/1986 | Conrow | 2/15 |
| 4,648,130 | 3/1987 | Kuznetz | 455/351 |
| 4,658,931 | 4/1987 | Curry | 381/187 |
| 4,682,374 | 7/1987 | Geiser | 2/209 |

Primary Examiner—Robert L. Griffin
Assistant Examiner—Curtis Kuntz

[57] ABSTRACT

The ear covering and eye covering assembly comprises an elongate curved band, first and second ear coverings mounted, respectively, to each end of the band, a molded plastic piece on the band, and an eye covering mounted to the plastic piece. If desired, a removable visor may be pivotably mounted on the plastic piece and radio speakers may be mounted within the ear coverings.

23 Claims, 2 Drawing Sheets

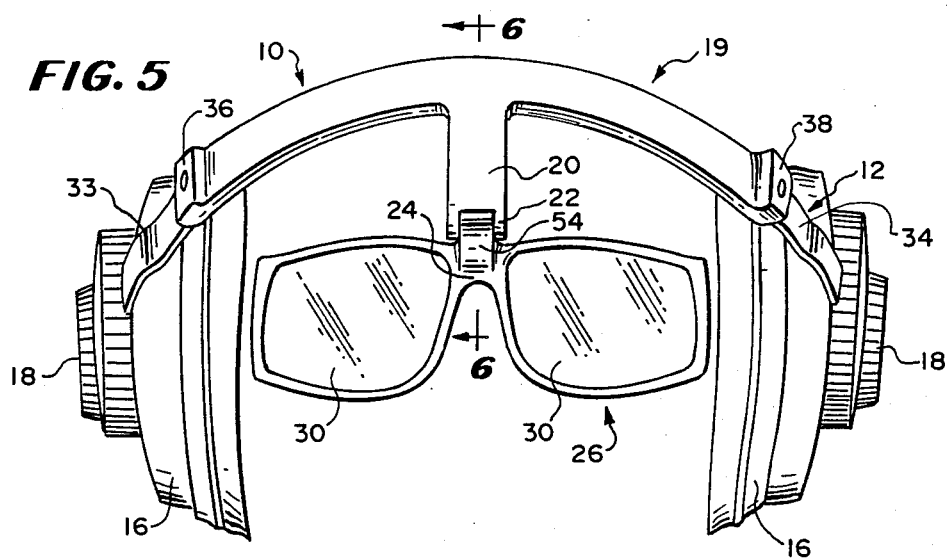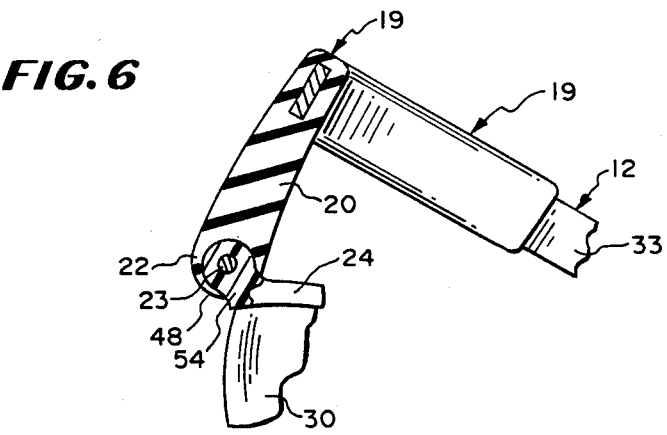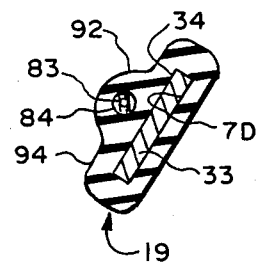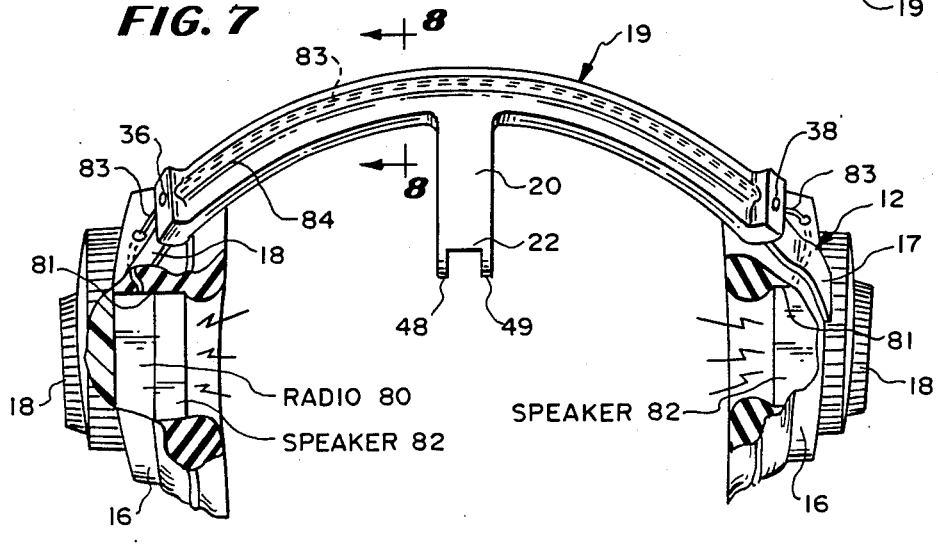

COMBINED EYE COVERING AND EAR COVERING ASSEMBLY

This is a continuation of application Ser. No. 889,747 filed July 28, 1986, now abandoned.

BACKGOUND OF THE INVENTION

1. Field of the Invention

The present invention relates to a combined eye covering and ear covering assembly particularly adapted for use in handgun target practice. More specifically, the invention relates to an assembly including a band which is positioned at an angle over the forehead and which is adapted to mount ear covering means and to mount eye covering means such as eyeglasses. If desired, a visor can be mounted to the assembly.

2. Description of the Prior Art

Heretofore various assemblies for covering ears and covering eyes have been provided.

For example, Rehman et al U.S. Pat. No. 3,108,282 discloses an ear defender and positioning apparatus for use with a helmet where each ear defender is mounted independently on the helmet, allowing for universal adjustment. Earphones may be provided within the ear defenders and a microphone may be provided to allow for a communication system.

Thomas U.S. Pat. No. 3,273,164 discloses a face shield assembly for a hard hat and a bracket for mounting a face shield on a safety helmet with the face shield being pivotable at locations to permit swinging of the shield from its working position to a position not substantially higher than the hat. The mounting bracket utilizes sound attenuator mounting means usually located within such safety helmet for fastening the shield to the hat while permitting optimum rotation of the face shield about pivoting means. Further, the bracket presents a bearing surface which serves as a stop for holding the shield in its proper working position in spaced relationship with the workman's face, with the mounting bracket being readily usable with "hard hats" of various sizes and configurations.

Leight U.S. Pat. No. 3,856,007 discloses an ear protector assembly which can be easily mounted on and removed from the temple bars of an eyeglass frame. The assembly comprises an arm having an inner end pivotably connected to the assembly and an ear plug fixed to an outer end of the arm. The assembly is provided with fasteners that enable one to clamp the assembly at any location along the temple bar where the ear plugs can be properly placed within the ears.

Heilberg U.S. Pat. No. 4,222,123 discloses a protective helmet with two externally located pockets for receiving fittings adapted to carry accessories. An elongate resilient arm in each fitting extends to the front of the helmet and forms one component in a pivot joint. Extending from the free ends of the elongate arms is a pivotably mounted face shield which may be flexed from a position of use to an upward, out of use position. Further, ear muffs are mounted on the protective helmet, with an external pocket for the face shield being positioned above the mounting for the ear muffs.

Karlsson et al U.S. Pat. No. 4,547,908 discloses a cap arrangement for sealing the space between the outer surface of a protective helmet and the upper edge of a pivotably mounted visor carried by the helmet to prevent, for example, sawdust from passing into the space on the inside of the visor during timber sawing operations. The cap arrangement comprises a sheet of fabric having a front edge secured to the upper edge of the visor and a rear edge secured to an elastic ribbon attached at its ends to mountings which pivotably support the visor at the sides of the helmet.

Kain U.S. Pat. No. Des 282,308 discloses a combined eye shade and ear protector.

As will be described in greater detail hereinafter, the combined ear covering and eye covering of the present invention comprises a simple resilient band that extends across the forehead of a wearer between ear coverings mounted at each end of the band and that has eye covering mounting means centrally positioned on the band and eye covering means mounted thereto for suspension over the eyes. Further, a visor may be mounted on the band for additional eye protection, such as from sunlight.

SUMMARY OF THE INVENTION

According to the present invention there is provided an ear covering and eye covering assembly comprising a resilient elongated curved head band structure adapted to be positioned at an angle over the wearer's forehead and having a middle portion and first and second end portions, each connected at one end to said middle portion, first and second ear coverings mounted, respectively, to one of said band structure end portions, means on said middle portion of said band structure for mounting an eye covering, and eye covering means mounted to said mounting means.

Further according to the invention, there is provided an ear covering and eye covering assembly comprising a resilient elongated head band structure adapted to be positioned at an angle over the wearer's forehead, first and second ear coverings mounted, respectively, to one end portion of said band structure, means on said band structure for mounting an eye covering, eye covering means mounted to said mounting means, and a removable visor pivotally mounted to said mounting means.

BRIEF DESCRIPTION OF THE DRAWINGS

FIG. 5 is a front elevational view of the the assembly shown in FIG. 1.

FIG. 6 is a fragmentary sectional view through the assembly and is taken along line 6—6 of FIG. 5.

FIG. 7 is a front elevational view of a further modified embodiment of the assembly with the eye covering removed and shows audio sound supplied through the ear coverings.

FIG. 8 is a fragmentary sectional view through the assembly shown in FIG. 7 and is taken along line 8—8 of FIG. 7.

DESCRIPTION OF THE PREFERRED EMBODIMENT

Figure 1:
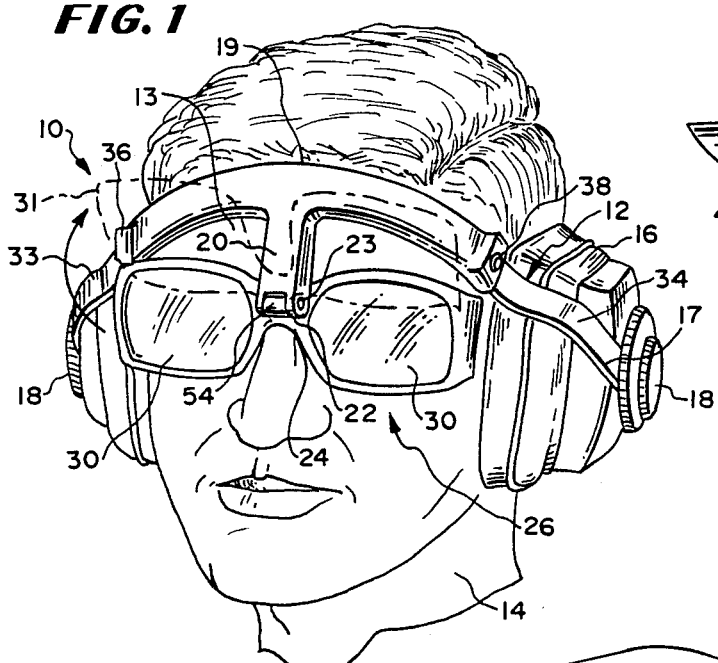
FIG. 1 is a perspective view of the ear covering and eye covering assembly of the present invention and shows the assembly mounted on a wearer's head.

Referring now to the drawings in greater detail, there is illustrated in FIG. 1 a combined ear covering and eye covering assembly 10 constructed according to the teachings of the present invention. As illustrated, the assembly 10 comprises a band 12 which is positioned to extend at an angle to the vertical across the forehead 13 of a wearer 14 and has an ear covering 16 at each end 17 of the band 12. Each ear covering 16 can be an ear muff with sound muffling material therein and is mounted inwardly of the end 17 of the band 12 by a knob 18 on the outer side of the end 17.

Mounted on the middle portion of the band 12 is a molded plastic piece or holder 19 having a projection 20 which includes a bifurcated end 22 which receives a pivot pin 23. A bridge portion 24 of an eye glass frame 26 forming the eye covering is pivotally mounted to the end 22. The frame 26, as illustrated, is not provided with temple bars but rather comprise only the frame 26 with lenses 30 mounted in the frame 26. As illustrated in phantom, the frame 26 can be rotated upwardly and off of the face of the wearer or user to a position designated by reference numeral 31.

In the illustrated embodiment, the band 12 includes two band sections 33 and 34 which overlap inside the plastic piece or holder 19 whereby the band sections 33 and 34 can be moved into and out of the holder 19 for adjusting the positions of the ear coverings 16.

Preferably, the band 12, namely the band sections 33 and 34, is made of a spring metal such as spring steel so that the band sections 33 and 34 urge the ear coverings 16 against the wearer's head.

Figure 2:
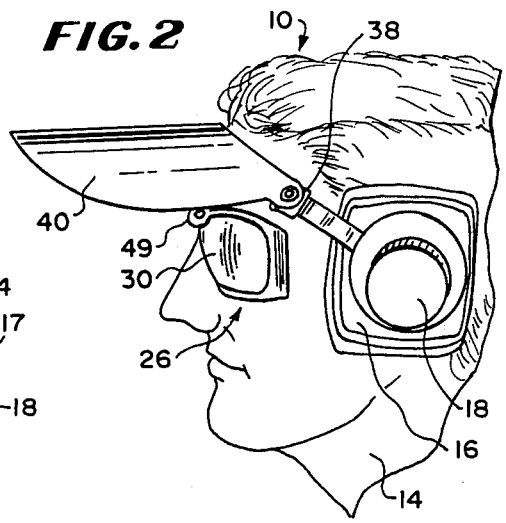
FIG. 2 is a side view of a modified embodiment of the assembly and shows a visor mounted on the assembly.

Turning now to FIG. 2, there is disclosed a modified embodiment of the combined ear covering and eye covering assembly 10 of the present invention. In this embodiment, positioned across the extent of the holder 19 and mounted at each raised end 36, 28 of the holder 19, is a visor 40 which is rotatable on the holder 19 from the position shown in FIG. 2 where it is used as a further sun shield for the eyes of the wearer to a rearwardly tipped position as shown in phantom in FIG. 4 at 42.

Figure 3:
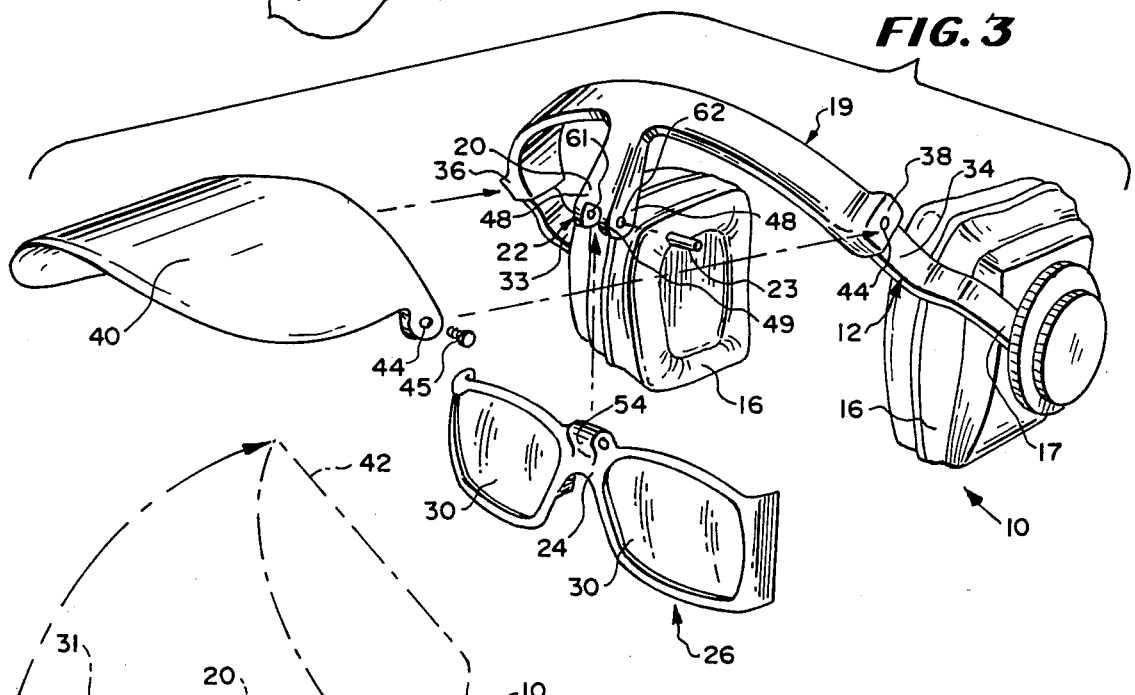
FIG. 3 is an exploded perspective view of the assembly shown in FIG. 2.

Turning now to FIG. 3, there is illustrated therein an exploded view of the assembly 10 with the visor 40.

As illustrated, each raised end 36, 38 of the holder 19 has a bore 44 within which is received a screw 45 for pivotally mounting one of two end flanges 46 of the visor 40 to the holder 19.

The downwardly extending projection 20 of the band 19 is provided at its free end 22 with two legs 48 and 49. A boss portion 54 of the eyeglass frame 26 extending upwardly and outwardly from the bridge 24 of the eye glass frame 26 is received between the legs 48 and 49. A pin 23 is pushed into and through bores 61 and 62 in the legs 48 and 49 and a bore 64 in the boss portion 54 above the bridge 24 of the eye glass frame 26 for pivotably connecting the frame 26 to the holder 19. Preferably, the boss portion 54 is sized to create a tight friction fit between the legs 48 and 49.

Figure 4:
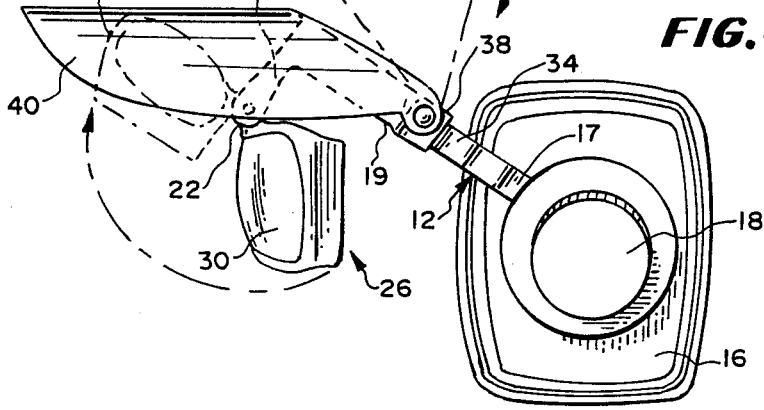
FIG. 4 is a side view of the assembly shown in FIG. 2 and shows eye glasses and the visor in a raised position, in phantom.

Turning now to FIG. 4, as illustrated in solid lines, the visor 40 and eye glass frame 26 of the assembly 10 are positioned to provide a shield for the eyes of the wearer 14. If perhaps, such as on a cloudy day, a wearer 14 of the assembly 10 would prefer not to utilize the visor 40, he would merely flip the visor 40 upwardly and position it above his head, out of the way, as illustrated in phantom in FIG. 4. Further, if the wearer 14 desires that the eyeglass frame 26 be out of the way as well, the frame 26 can be rotated upwardly around the hinge pin 23 and can be positioned away from the face as illustrated in phantom in FIG. 4.

Referring now to FIG. 5, there is illustrated therein the combined ear covering and eye covering assembly 10, with the visor 40 removed, and shows a view similar to that illustrated in FIG. 1.

Here it is more easily seen that the ear coverings 16 are each mounted on respective spring band sections 33 and 34 with the spring band sections 33, 34 being movable independently of one another within the piece or holder 19 (FIG. 8).

In this way, one can adjust the position of each ear covering 16 relative to the holder 19 to maintain the center of the holder 19 centrally positioned on a wearer's forehead 13 while assuring good fit of the ear coverings 16 over the wearer's ears.

Alternatively the band 12 can be of unitary construction and each ear covering 16 can be pivotally mounted to a slidable holder slidably received on an end 17 of the band 12 for adjustably positioning the ear covering 16. is formed integral with the holder 12. Further, as illustrated in FIG. 6, the spring band sections 33 and 34 which mount the ear coverings are received in a slot 70 in the holder 12.

Also, the mounting of the boss portion 54 by means of the pin 23 is shown in FIG. 6.

Since the band 12 is pivotably mounted to the ear coverings 16 and knobs 18, the band 12 can be moved arcuately up or down relative to the wearer's forehead 13 for proper, comfortable positioning of the eyeglass frame 26 for the individual wearer of the assembly 10.

Turning now to FIG. 7, there is illustrated therein an embodiment of the assembly 10 wherein the feature of audio capabilty is added to the assembly 10.

As illustrated, a radio 80 is mounted within a cavity 81 of one ear covering 16 and speakers 82 are provided in each cavity 81. Wire conductors 83 (only one of which is shown) extend from the radio 80 in one ear covering 16 through a slot 84 provided in the holder 19 of the assembly 10 to the speaker 82 in the other ear covering 16.

The radio 80 or a tape player could be carried in a pocket of the wearer and connected by wire conductors (not shown) to the speakers 82.

Alternatively, audio tubes could be connected to the cavity 82 from a radio 80 in one cavity 81 or from a radio carried in a shirt pocket.

Referring now to FIG. 8, there is illustrated therein a cross-section through the holder 19 of the assembly 10 and shows that the slot 84 may be incorporated into a slightly modified holder 19 which, rather than being generally rectangular in cross-section, is provided with a raised area 92 along an outer elongate surface 94 thereof within which the slot 84 is provided. The wire conductors 83 for the audio system are fed through the slot 84 to connect the speaker 82 in one ear covering 16 to the radio 80.

The assembly 10 described above has a number of advantages. For example, the assembly 10 is unitary. Further, since the eyeglass frame 26 is mounted on the wearer's head without need of temples, no pain is caused the wearer by the ear protectors forcing such temples against the skull as is usually incurred when one wears ear protectors with regular glasses.

Also, since no eyeglass temples are encountered, gaps in the seal of the ear protector against the wearer's head are eliminated.

Further, since a visored cap is difficult to maintain on a wearer's head when ear protectors are utilized (because of the band 12 extending across the top of the head) the need for a visored cap is eliminated by the provision of the optional visor 40 of the assembly 10.

Also, modifications can be made to the assembly of the present invention without departing from the teachings of the present invention. For example, the eyeglass lenses 30 can be tinted or prescription lenses. Alternatively, the frame 26 and lenses 30 can be replaced by a unitary, one piece molded glass or plastic eye covering.

Accordingly, the scope of the invention is only to be limited as necessitated by the accompanying claims.

I claim:

1. An ear covering and eye covering assembly comprising a resilient, hard, stiff, non-elastic, arcuate, non-encircling elongated head band structure which is adapted to be positioned at an angle above the eyes and across a forehead of a wearer and which is constructed to extend only part way around the head of a wearer from one ear forwardly across the forehead to the other ear and not behind the head or over the top of the head of the wearer, said band structure having a hard, inelastic center portion which is adapted to be positioned over the middle of the forehead of the wearer and above the nose of the wearer and first and second hard, inelastic, but flexible end portions each having a free end which is arranged to extend to a position adjacent one ear, each end portion including a band made of rigid but flexible spring material and coupled at an inner end thereof, opposite said free end, to said center portion of said band structure, first and second ear coverings mounted, respectively, to one of said band structure end portions adjacent said free end thereof, adjusting means for adjusting the position of said ear coverings on said band end portions, said center portion of said band structure including rigid mounting means centrally located over the wearer's forehead for mounting an eye covering, and an eye covering mounted to said mounting means.

2. The assembly of claim 1 wherein said eye covering mounting means is a molded plastic piece received on said band structure.

3. The assembly of claim 1 wherein said eye covering means is pivotably mounted to said mounting means.

4. The assembly of claim 1 wherein said head band structure includes a spring metal member extending to and including said end portions of said band structure whereby said ear coverings are urged against the wearer's head.

5. The assembly of claim 1 wherein said eye covering includes an eye glass frame and a pair of lenses mounted in said frame.

6. The assembly of claim 5 wherein said eyeglass frame is pivotably mounted to said mounting means.

7. The assembly of claim 5 wherein said lenses are clear.

8. The assembly of claim 5 wherein said lenses are tinted.

9. The assembly of claim 5 wherein said lenses are prescription glasses.

10. The assembly of claim 1 wherein said eye covering comprises a one piece molded construction eye covering.

11. The assembly of claim 10 wherein said eye covering is made of safety glass or plastic.

12. The assembly of claim 1 further including a removable visor mounted on said mounting means.

13. The assembly of claim 12 wherein said visor is pivotably mounted to said mounting means.

14. The assembly of claim 1 wherein each ear covering has an audio delivery means therein.

15. The assembly of claim 14 wherein said audio delivery means comprise at least one speaker mounted in one of said ear coverings.

16. The assembly of claim 15 wherein each ear covering has a speaker therein.

17. The assembly of claim 15 wherein said audio delivery means include a radio.

18. The assembly of claim 17 wherein each ear covering has a speaker therein and said assembly includes wire conductors carried by said mounting means and connected between said speakers and said radio.

19. The assembly of claim 1 wherein said ear covering includes sound muffling means.

20. The assembly of claim 1 wherein said center portion of said band structure is arcuate, non-encircling and tubular and adapted to receive therein said band of each end portion of said band structure which are slidable frictionally within said center portion of said band structure, said frictional slidable mounting of said bands within said arcuate, tubular, center portion of said band structure defining said adjusting means for adjusting the position of said ear coverings.

21. The assembly of claim 1 wherein each ear covering is pivotally mounted to one of said band structure end portions.

22. The assembly of claim 1 wherein said adjusting means includes slide mounting means on each ear covering for slidably mounting each ear covering on one of said band structure end portions.

23. An ear covering and eye covering assembly comprising a resilient, hard, stiff, non-elastic, arcuate, non-encircling elongated head band structure which is adapted to be positioned at an angle above the eyes and across a forehead of a wearer and which is constructed to extend only part way around the head of a wearer from one ear forwardly across the forehead to the other ear and not behind the head or over the top of the head of the wearer, said band structure having a hard, inelastic center portion which is adapted to be positioned over the middle of the forehead of the wearer and above the nose of the wearer and first and second hard, inelastic, but flexible end portions each having a free end which is arranged to extend to a position adjacent one ear, first and second ear coverings mounted, respectively, to one of said end portions of said band structure adjacent said free end thereof, said center portion of said band structure including hard, inelastic, rigid mounting means centrally located over the wearer's forehead for mounting an eye covering, and an eye covered mounting to said mounting means.

* * * * *